United States Patent

Berg et al.

[11] Patent Number: 6,123,168
[45] Date of Patent: Sep. 26, 2000

[54] BANDED HEARING PROTECTOR

[75] Inventors: Bengt Göran Berg; Hans Peter Jörgen Håkansson, both of Tyringe, Sweden

[73] Assignee: Dalloz Safety AB, Billesholm, Sweden

[21] Appl. No.: 08/885,918

[22] Filed: Jun. 30, 1997

[30] Foreign Application Priority Data

Jul. 3, 1996 [DE] Germany ............... 296 11 562 U

[51] Int. Cl.⁷ ........................... H04R 25/00
[52] U.S. Cl. ............... 181/129; 128/866; 2/209
[58] Field of Search ................. 181/129, 130, 181/131, 135; 381/183, 187; 2/209; 128/864, 866, 867

[56] References Cited

U.S. PATENT DOCUMENTS

| | | |
|---|---|---|
| Re. 30,861 | 2/1982 | Krawagna . |
| 186,422 | 1/1877 | Hackett et al. ............... 2/209 |
| D. 241,881 | 10/1976 | Peterson et al. . |
| D. 245,202 | 7/1977 | Asker . |
| D. 269,611 | 7/1983 | Saito . |
| D. 292,530 | 10/1987 | Andersson . |
| D. 331,966 | 12/1992 | Gardner, Jr. . |
| 2,498,960 | 2/1950 | Mullin ................. 181/135 |
| 2,780,681 | 2/1957 | Shaper ................. 181/135 |
| 3,288,246 | 11/1966 | Allen . |
| 3,301,253 | 1/1967 | Glorig ................. 181/135 |
| 3,319,736 | 5/1967 | Reynolds, Jr. . |
| 3,339,667 | 9/1967 | Speelman . |
| 3,720,979 | 3/1973 | Krawagna . |
| 4,671,265 | 6/1987 | Andersson ............. 2/209 |
| 5,059,017 | 10/1991 | Bennato . |
| 5,438,626 | 8/1995 | Neuman et al. . |

FOREIGN PATENT DOCUMENTS

| | | |
|---|---|---|
| 587925 | 3/1994 | European Pat. Off. . |
| 922264 | 3/1963 | United Kingdom . |
| 1355052 | 5/1974 | United Kingdom . |

OTHER PUBLICATIONS

English language abstract of European Patent Application No. 587 925.

*Primary Examiner*—Khanh Dang
*Attorney, Agent, or Firm*—Greenblum & Bernstein, P.L.C.

[57] ABSTRACT

Banded hearing protector that includes two hearing protecting bodies of soft, sound attenuating material and a headband including a central part having two ends and headband shanks having angled ends. Each angled end may support one of the two hearing protecting bodies. The banded hearing protector may also include a hinge that swingably couples each of the headband shanks to the central part and each of the two hearing protecting bodies may include a convexly curved contact surface positioned opposite the angled ends.

22 Claims, 2 Drawing Sheets

BANDED HEARING PROTECTOR

CROSS-REFERENCE TO RELATED APPLICATION

The present application claims priority under 35 U.S.C. § 119 of German Patent Application No. 296 11 562.2, filed Jul. 3, 1996.

BACKGROUND OF THE INVENTION

1. Field of the Invention

The present invention relates to a banded hearing protector having two hearing protecting bodies of soft, sound attenuating material at the two opposite angled ends of an elastic headband to protect the human ear from annoying and harmful noise.

2. Discussion of Background Information

In the prior art, spacious ear muffs that cover the wearer's ears provide extensive noise protecting effect, however, such hearing protectors require so much space that they will not generally fit into the wearer's pocket when not in use. In other words, these hearing protectors are not intended for being easily stored in the users pocket, i.e., to be put on either frequently or occasionally, when a hearing protector is desired or required.

U.S. Design Pat. No. D 331,966 discloses a banded hearing protector having rounded hearing protecting bodies of soft, sound attenuating material at the ends of a one-piece elastic headband. However, this headband is so large, i.e., generally the width of the wearer's head, that it cannot be easily stored in a pocket when not in use.

U.S. Design Pat. No. D 292,530 discloses a banded hearing protector that is foldable for convenient storage in a pocket. The ends of this banded hearing protector are provided with relatively long and narrow, tapered earplugs that are to be inserted into the ear canal. A hinge of the headband of the hearing protector has a film hinge part and an interlockable protrusion/groove part.

SUMMARY OF THE INVENTION

The present invention relates to a banded hearing protector of the type generally discussed above. Due to the foldability feature of the present invention, the banded hearing protector may be easily carried in a pocket of a shirt, slacks, dress, jacket, etc., and may be quickly and comfortably put on and taken off from the wearer's head.

According to the present invention, the headband may include a central part having hinged ends coupled to respective foldable band shanks of the headband and hearing protecting bodies located at opposite ends of the headband may have convexly curved contact surfaces.

A foldable headband with hearing protecting bodies having a convexly curved contact surface provides very easy and comfortable handling. The prior art hearing protecting bodies which are in the shape of earplugs to be inserted in the ear canal have to be inserted into the ear canal from a fixed, predetermined direction. This is not necessary with the present invention because the hearing protecting body has a convexly curved contact surface that may be pressed against the ear from almost any direction. The banded hearing protector of the present invention may be put on with only one hand. For example, one end of the band may be unfolded and the attached hearing protecting body may be pressed against the wearer's ear. Then, the second band shank of the hearing protector may be unfolded with the one hand. This manner of putting on the banded hearing protector of the present invention, e.g., even with pivoting motions of the band and the hearing protecting body already positioned in the first ear, substantially eliminates any disturbing or unfavorable feeling for the wearer. Thus, the second band shank may be unfolded by the one hand to forward the other hearing protector body to the second ear. Similarly, the banded hearing protector can be taken off by one hand, e.g., the hand closest to the ear, generally with a pivoting motion.

The contact surface of the hearing protector bodies is, preferably, approximately semi-globular, while the pressure exerted against the ear by the ends of the headband may be almost the same in all positions.

According to one preferred embodiment of the present invention, the banded hearing protector may be formed of a single piece of plastic and each hinge of the headband, e.g., on an inside of the band, may be a film hinge. The axis of the film hinge may extend substantially perpendicular to a plane of the headband. Further, the hinge may include two interlocking hinge parts located over the film hinge, such that, in an unfolded position, the interlocking parts have complementary surfaces that fit to each other. One of the hinge parts may include a projecting protrusion that fits into a groove located in the other hinge part.

The engagement of the two hinge parts, i.e., the protrusion into the groove, results in an unfolded or open position of the headband in which the headband achieves a bow stiff connection in all directions between the central part of the headband and the band shanks. In this manner, any bending stress that may arise while the banded hearing protector is being put on and taken off, e.g., with only one hand, and/or may arise across the surfaces of the headband may be transferred to the headband hinge without any risk of damage.

According to a preferred embodiment of the present invention, the protrusion may include a slide blade that has two sides positioned substantially parallel to the headband plane and the groove may include a slit shape to accomodate the slide blade that includes two side surfaces to be in close, i.e., abutting or with a small space, contact with the sides of the slide blade, when the headband is unfolded. Thus, a very rigid connection may be achieved in the hinge area Further, the side surfaces of the groove may be positioned to be substantially parallel to each other and to the headband plane.

The present invention is therefore be directed to a banded hearing protector. The banded hearing protector preferably includes two hearing protecting bodies of soft, sound attenuating material and a headband including a central part having two ends and headband shanks having angled ends. Each angled end may support one of the two hearing protecting bodies. The banded hearing protector may also include a hinge that swingably couples each of the headband shanks to the central part and each of the two hearing protecting bodies may include a convexly curved contact surface positioned opposite the angled ends.

According to another feature of the present invention, the contact surface may include an approximately semi-globular surface.

According to still another feature of the present invention, the headband may be composed of a single piece of plastic. The hinge may include a film hinge on an inside surface of the headband, a hinge axis substantially perpendicular to a plane including the central part and the headband shanks, and two hinge parts coupled to each other over the film hinge. The two hinge parts may have contact surfaces that are positioned close to each other when the headband is in an unfolded position. One of the two hinge parts may include a projecting guiding protrusion and the other of the two hinge parts may include a guiding groove. At least in the unfolded position of the headband, the projecting guiding protrusion may fit into the guiding groove.

According to a still further feature of the present invention, an outer edge of the slide blade may be approximately perpendicular to the hinge axis and may be located outside of the guiding slit, when the headband is in a folded position.

According to another feature of the present invention, the headband may be made of an elastic material. Further, the elastic material may preferably comprise polypropylene.

According to still another feature of the present invention, the headband shanks may include an angular portion and the headband shanks may be coupled to the central part such that ends of the headband shanks opposite the hinges are angled toward each other. Further, an angle of the angular portion, e.g., α, may be between approximately 125° and 175°, preferably may be between approximately 135° and 160°, most preferably between approximately 145° and 155°, and with a preferred angle being approximately 150°, and an angle of the angled end, e.g., β, may be between approximately 75° and 125°, preferably may be between approximately 90° and 115°, most preferably between approximately 95° and 105°, and with a preferred angle being approximately 100°.

The present invention may also be directed to a banded hearing protector that includes a central portion, shanks extending from the central portion, and hinges that couple the shanks to the central portion. The shanks may include angled portions and the hinges may provide an inward bias on the shanks. The banded hearing protector may also include end caps coupled to ends of the shanks opposite the hinges and the end caps may be positionable over the ear canal.

According to another feature of the present invention, the angled portions may be positioned such that a distance between the end caps may be less than a distance between the hinges.

According to another feature of the present invention, the angled portions may be angled inwardly such that, when the banded hearing protector is opened, the end of the shanks may be located within an arc formed by the central part.

According to a still further feature of the present invention, the hinges may include a film hinge coupling a first hinge part to a second hinge part.

According to another feature of the present invention, the first hinge part may include a first contact surface and a protrusion extending from the first contact surface and the second hinge part may include a second contact surface and a groove extending into the second contact surface. The protrusion may be insertable into the groove.

According to a further feature of the present invention, when the banded hearing protector is open, the first and second contact surfaces may be positioned substantially parallel to each other and the protrusion extends into the groove. Further, when the banded hearing protector is closed, the protrusion does not extend into the groove.

According to yet another feature of the present invention, the protrusion may have a wedge shape and may extend parallel to a plane including the central portion and the shanks formed by the banded hearing protector. Further, the protrusion may be slidable within the groove.

Other exemplary embodiments and advantages of the present invention may be ascertained by reviewing the present disclosure and the accompanying drawing figures.

BRIEF DESCRIPTION OF THE DRAWINGS

The present invention may be further described in the detailed description which follows, in reference to the noted plurality of drawings by way of non-limiting examples of preferred embodiments of the present invention, in which like reference numerals represent similar parts throughout the several views of the drawings, and wherein.

DETAILED DESCRIPTION OF THE PREFERRED EMBODIMENTS

Figure 1:
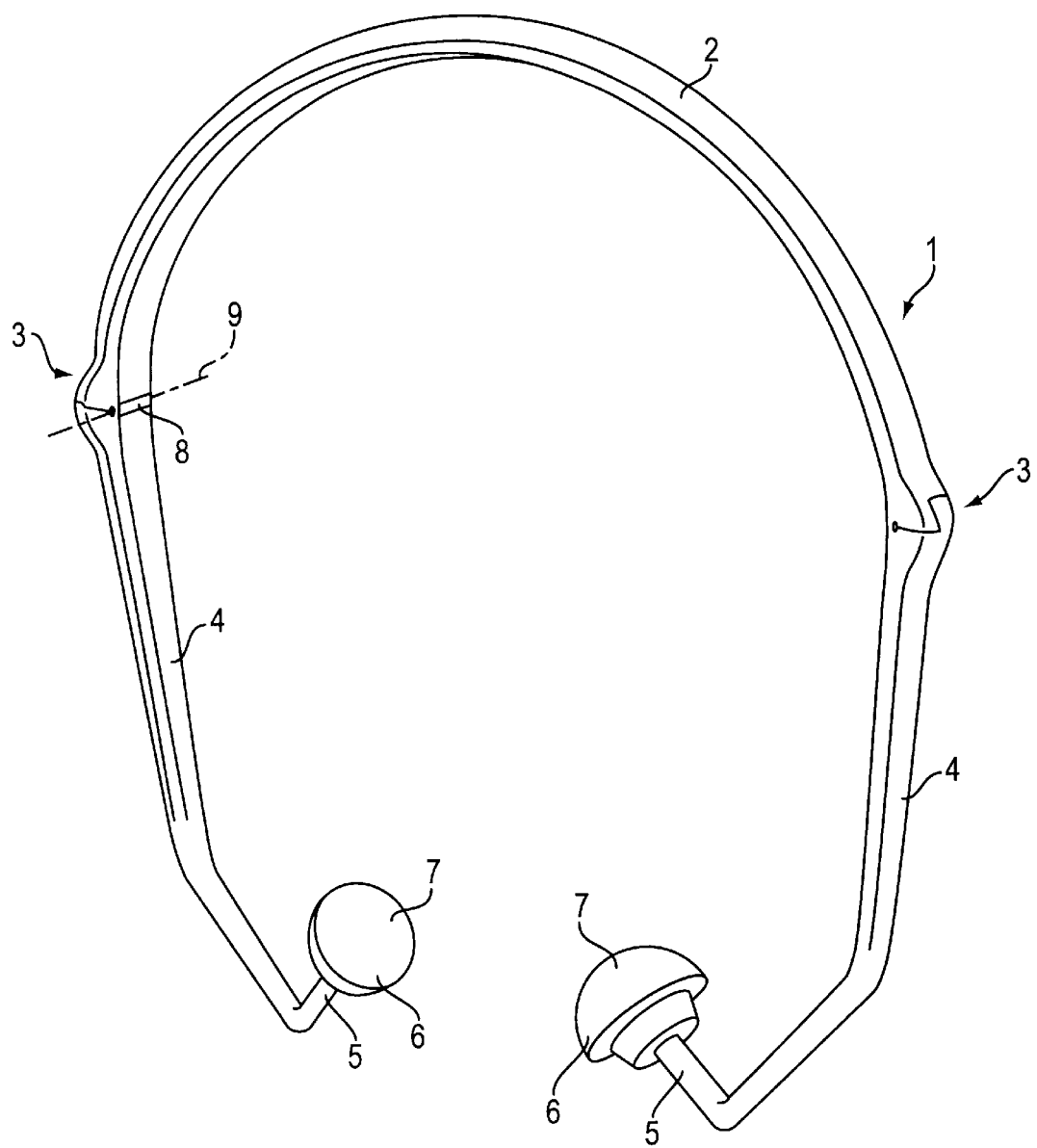
FIG. 1 illustrates a banded hearing protector in an unfolded position.

The particulars shown herein are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for the fundamental understanding of the invention, the description taken with the drawing figures making apparent to those skilled in the art how the invention may be embodied in practice.

Figure 2:
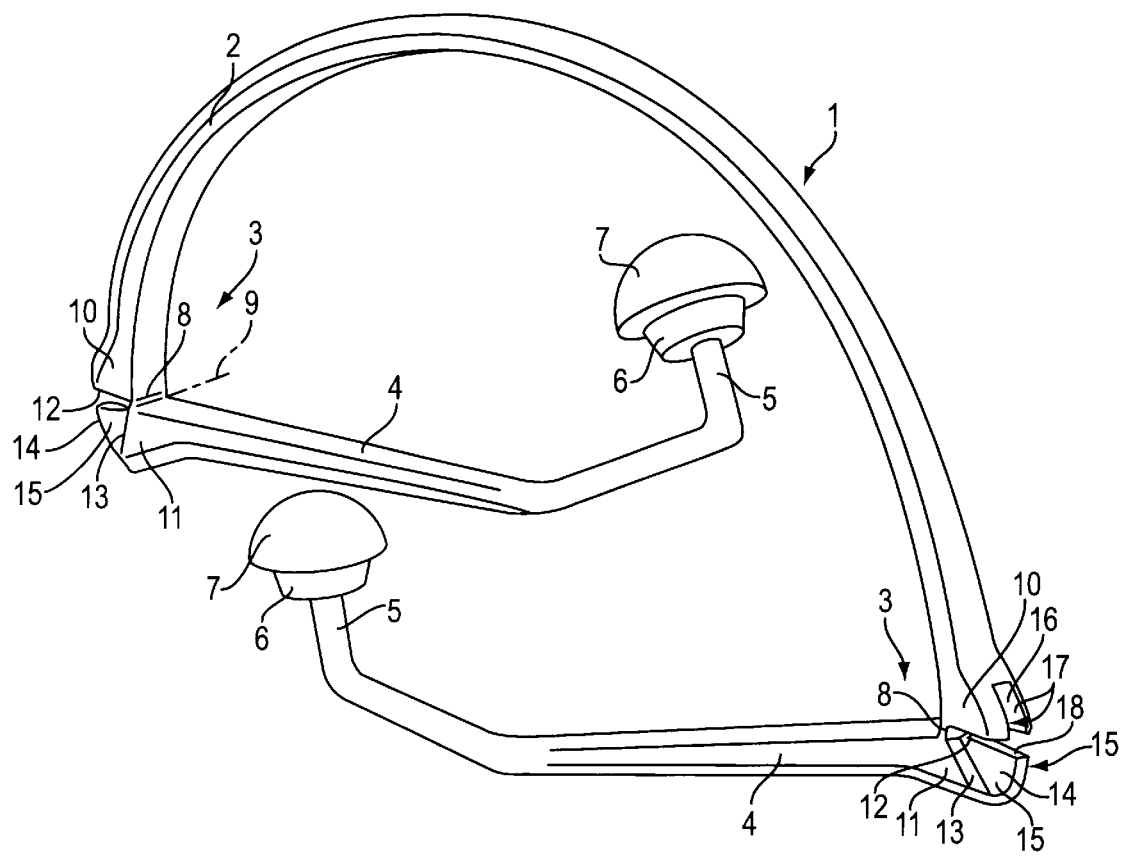
FIG. 2 illustrates the banded hearing protector depicted in FIG. 1 in a storage (folded) position.

A banded hearing protector according to the present invention is illustrated in FIGS. 1 and 2. The banded hearing protector includes an elastic band 1 manufactured as a single piece of plastic, preferably polypropylene, which may be utilized as a headband or chin band for the user. A central part 2 of elastic band 1 may be coupled to two headband shanks 4 via headband hinges 3. An end of headband shanks 4 opposite headband hinges 3 may be inwardly angled at a predetermined angle a and may be angled again at an angle β to form a headband end 5 as a support member for a hearing protecting body (end caps) 6 which may be a soft, sound attenuating material, e.g., foam plastic.

Hearing protecting bodies 6 may include an approximately semi-globular convex contact surface 7 disposed on a side opposite headband end 5. Hearing protector bodies 6 may be provided for flexible contact with the ear in an area of the orifice of the ear canal, however, semi-globular convex contact surface 7 is of a size greater than the ear canal so that hearing protecting bodies cover the ear canal and are not inserted into the ear canal.

Headband hinges 3 may be provided with a film hinge 8 on an inside surface of the headband. Further, film hinge 8 may pivot around a hinge axis 9 which is positioned perpendicular to a plane formed by the headband. Headband hinge 3 preferably includes two hinge parts 10 and 11 which are coupled to each other at least through film hinge 8. Headband hinge 3 may be thickened with respect to the headband to form nodes when the headband is unfolded (open). Hinge parts 10 and 11 may be shaped such that, when unfolded, they form the nodes in the headband where central part 2 and headband shank 4 are coupled together. Hinge parts 10 and 11 may include contact surfaces 12 and 13, respectively, which may radially extend from hinge axis 9 of film hinge 8 and may be positioned close to each other (adjacent to and/or contacting each other) when the headband is in the unfolded position.

Hinge part 11 may include a slide blade 14 that protrudes from contact surface 13 and divides the contact surface 13 into two side sections. Slide blade 14 may include a side surface 15 on each of its two sides profiled to extend parallel to the headband plane.

Hinge part 10 may include a guiding slit 16 formed within contact surface 12. Guiding slit 16 may be shaped to fit slide blade 14. Guiding slit 16 may include two inner surfaces 17 which may be profiled to extend parallel to each other and to the headband plane.

Hinge 3 biases hearing protecting bodies 6 toward each other to improve the sealing of the ear canal and to indirectly provide better attenuation. Thus, when in the unfolded (open) position, the headband may be prestressed with an inward bias. The angle within headband shanks 4 may be provided to accomodate the wearer's ear, i.e., to provide sufficient room inside the headband for the ear. This angle also prevents undesired contact or pressing of the ear against headband shank 4 which may interfere with the sealing of the ear canal and the attenuation. The inward angle α of headband shank 4 may be, e.g., between approximately 125° and 175°, preferably may be between approximately 135° and 160°, most preferably between approximately 145° and 155°, and with a preferred angle being approximately 150°. However, the specific angle may be selected by considering the characteristics of the material of the headband, the contoured shape of the ear plug, and the desired sealing of the ear. Further, the angle β forming the headband end 5 may be, e.g., between approximately 75° and 125°, preferably may be between approximately 90° and 115°, most preferably between approximately 95° and 105°, and with a preferred angle being approximately 100°.

As is shown in FIG. 2, slide blade 14 may be substantially wedge-shaped and may include an outer edge 18 that may be approximately perpendicular to hinge axis 9 and that may be outside guiding slit 16 when the headband is in a folded (closed) position. When folding the headband, headband shank ends 5 may be brought toward central part 2, when unfolding the headband, headband shank ends 5 are pulled downward to form a substantially continuous substantially arcuate headband. When unfolding, slide blade 14 may slidably penetrate guiding slit 16, e.g., which brings hinge parts 10 and 11 towards each other until contact surfaces 12 and 13 are substantially parallel to each other and/or contact each other. Thus, during the sliding penetration of slide blade 14 in guiding slit 16, the side surfaces 15 may slidably engage inner walls 17 by contact or a small gap may be maintained between side surfaces 15 and inner walls 17. The relation between the side surfaces 15 and inner walls 17 stabilizing hinge 3 while preventing damage due to forces transverse to the direction of hinge movement. Further, even when the headband is positioned in a partially unfolded position, a portion of slide blade 14 may penetrate guiding slit 16. In this manner, tension forces and forces exerted transverse to the headband plane may still be overcome.

In accordance with the above discussed arrangement, the headband of the present invention may be worn over the head, under the chin, and/or behind the neck.

It is noted that the foregoing examples have been provided merely for the purpose of explanation and are in no way to be construed as limiting of the present invention. While the invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the invention in its aspects. Although the invention has been described herein with reference to particular means, materials and embodiments, the invention is not intended to be limited to the particulars disclosed herein; rather, the invention extends to all functionally equivalent structures, methods and uses, such as are within the scope of the appended claims.

What is claimed:

1. A banded hearing protector comprising:

two hearing protecting bodies of soft, sound attenuating material;

a headband comprising a central part having two ends and headband shanks having angled ends, each angled end supporting one of the two hearing protecting bodies;

a hinge that swingably couples each of the headband shanks to the central part; and each of the two hearing protecting bodies comprising a convexly curved contact surface positioned opposite the angled ends.

2. The banded hearing protector according to claim 1, the contact surface comprising an approximately semi-globular surface.

3. The banded hearing protector according to claim 1, the headband being composed of a single piece of plastic.

4. The banded hearing protector according to claim 3, the hinge comprising a film hinge on an inside surface of the headband; a hinge axis substantially perpendicular to a plane including the central part and the headband shanks; and two hinge parts coupled to each other over the film hinge;

the two hinge parts having contact surfaces that are positioned close to each other when the headband is in an unfolded position;

one of the two hinge parts comprising a projecting guiding protrusion; and another of the two hinge parts comprising a guiding groove, wherein, at least in the unfolded position of the headband, the projecting guiding protrusion fits into the guiding groove.

5. The banded hearing protector according to claim 4, the projecting guiding protrusion comprising a slide blade having two side surfaces substantially parallel to the headband plane;

the guiding groove comprising a guiding slit that matches the slide blade and has two inner surfaces; and the slide blade fitting between the two inner surfaces in an unfolded position of the headband.

6. The banded hearing protector according to claim 5, the two inner surfaces of the guiding slit being positioned to be substantially parallel to each other and to the headband plane.

7. The banded hearing protector according to claim 5, an outer edge of the slide blade being approximately perpendicular to the hinge axis and being located outside of the guiding slit, when the headband is in a folded position.

8. The banded hearing protector according to claim 1, the headband being made of an elastic material.

9. The banded hearing protector according to claim 8, the elastic material comprising polypropylene.

10. The banded hearing protector according to claim 1, the headband shanks further having angular portions; and the headband shanks being coupled to the central part such that angled ends of the headband shanks opposite the hinges are angled toward each other.

11. The banded hearing protector according to claim 10, an angle of the angular portion being between approximately 125° and 175°.

12. The banded hearing protector according to claim 11, an angle of the angled ends being between approximately 75° and 125°.

13. A banded hearing protector comprising:

a central portion;

shanks extending from the central portion, said shanks including angled portions;

hinges coupling the shanks to the central portion and providing an inward bias on the shanks; and end caps coupled to ends of the shanks opposite the hinges, said end caps being positionable over the ear canal.

14. The banded hearing protector according to claim 13, said angled portions positioned such that a distance between said end caps is less than a distance between said hinges.

15. The banded hearing protector according to claim 13, said angled portions being angled inwardly, wherein, when the banded hearing protector is opened, said end of each shank is located within an arc formed by said central part.

16. The banded hearing protector according to claim 13, said angled portions having an angle of between approximately 125° and 175°.

17. The banded hearing protector according to claim 13, said hinges comprising a film hinge coupling a first hinge part to a second hinge part.

18. The banded hearing protector according to claim 17, said first hinge part including a first contact surface and a protrusion extending from said first contact surface;

said second hinge part including a second contact surface and a groove extending into said second contact surface; and said protrusion being insertable into said groove.

19. The banded hearing protector according to claim 18, wherein, when said banded hearing protector is open, said first and second contact surfaces are positioned substantially parallel to each other and said protrusion extends into the groove.

20. The banded hearing protector according to claim 18, wherein, when said banded hearing protector is closed, said protrusion does not extend into said groove.

21. The banded hearing protector according to claim 18, said protrusion having a wedge shape and extending parallel to a plane formed by said banded hearing protector.

22. The banded hearing protector according to claim 18, said protrusion being slidable within said groove.

* * * * *